United States Patent [19]

Itagaki et al.

[11] Patent Number: 5,866,146

[45] Date of Patent: Feb. 2, 1999

[54] COMPOSITIONS FOR FAIR-SKIN

[75] Inventors: Yasuharu Itagaki; Morimasa Tanimoto; Seiji Kurosawa; Tetsuro Ohba, all of Sapporo, Japan; Klaas Doesburg, Hoogezand, Netherlands; Jan Sikkema, Zeegse, Netherlands; Taisuke Iwasaki, Hoogezand, Netherlands

[73] Assignee: Snow Brand Milk Products Co., Ltd., Sapporo, Japan

[21] Appl. No.: 804,821

[22] Filed: Feb. 24, 1997

[30] Foreign Application Priority Data

Mar. 13, 1996 [JP] Japan ................... 8-084774

[51] Int. Cl.$^6$ .................... A61K 7/00; A61K 7/48; A61K 31/715

[52] U.S. Cl. ................... 424/401; 424/488; 424/493; 514/54; 435/101

[58] Field of Search .................... 424/401, 488, 424/493; 435/101; 514/54

[56] References Cited

U.S. PATENT DOCUMENTS 5,568,580  8/1997  Mausner ................... 424/401

FOREIGN PATENT DOCUMENTS

| 2682596 | 4/1993 | France . |
|---|---|---|
| 59-122413 | 7/1984 | Japan . |
| 94/12656 | 6/1994 | WIPO . |

OTHER PUBLICATIONS

Nakajima et al. 1992 Carbohydrate Research vol. 224, pp. 245–253, Jan. 1992.

XP 002033169—Derwent Publications Ltd., London, GB—AN 203617 & JP 03 127 713 A (Sansho Pharm Co) 30.

XP 002033170—Derwent Publications Ltd., London, GB—AN 361894 & JP 04 264 016 A (Yakult Honsha KK) 18.

*Primary Examiner*—Michael P. Woodward
*Assistant Examiner*—Mary K Zeman
*Attorney, Agent, or Firm*—Burgess, Ryan & Wayne

[57] ABSTRACT

This invention provides compositions for fair-skin containing the phosphorylated polysaccharides produced by lactic acid bacteria as an effective ingredient. The phosphorylated polysaccharides are expressed, for example, by the following formula and contained in the compositions for fair-skin at concentrations of 0.01–20 weight % and are used such as creams, emulsions and toilet lotions.

The compositions for fair-skin exhibit fair-skin effect by inhibiting activities to melanoma proliferation and melanin formation.

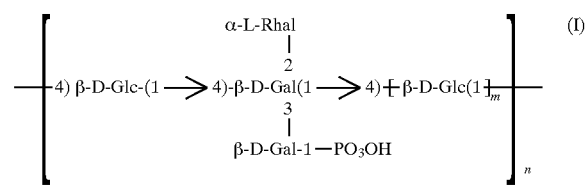

(wherein, Glc, Gal and Rha represent glucose, galactose and rhamnose residues, respectively. Numerals shown by other than subscript represent the respective binding sites and n represents the degree of polymerization of 1,000–5,000).

10 Claims, 3 Drawing Sheets

COMPOSITIONS FOR FAIR-SKIN

FIELD OF THE INVENTION

This invention relates to compositions for fair-skin composed of phosphorylated polysaccharides produced by lactic acid bacteria as an effective ingredient.

BACKGROUND OF THE INVENTION

Spots and freckles on human skin have been known to be caused by formation of melanin in skin tissues due to sunburn or the like. Also, formation of melanin through several steps from tyrosine by enzymic oxidation with a tyrosinase is known. Thus, suppression of spots and freckles in human skin can be attained by inhibition of tyrosinase activity. Tyrosinase inhibitory substances such as arbutin, kojic acid and casein hydrolysates are known and have been used as effective ingredients in compositions for human fair-skin up to date. Furthermore, novel substances which can inhibit tyrosinase activity and be used as an effective ingredient for human fair-skin are now under investigation.

In addition, various polysaccharide producing lactic acid bacteria are also known. Some lactococci such as *Streptococcus lactis, Lactoncoccus lactis, Streptococcus cremoris* and *Lactococcus cremoris* have been reported to produce phosphorylated polysaccharides (Japanese published unexamined patent application No. 229702 (1991); Nakajima et al., Carbohydr. Res., 224, pp. 245–253 (1992)). Furthermore, some lacobacilli such as *Lactobacillus sake* are also reported to produce phosphorylated polysaccharides (WO94/12656). All these phosphorylated polysaccharides have repetitive definite sequences of sugar chain of monosaccharides such as glucose, galactose and rhamnose bound directly or indirectly through the other monosaccharide with phosphoric acid residue in monosaccharide or glycerol residue as a side chain, and are different from neutral polysaccharides. Two of three oxy-acids in the phosphoric acid residue participate in the ester bindings with monosaccharides, and one remains free and can participate in the reaction with the other compounds.

The inventors of the present invention have been eagerly investigating for a compound which can be used as an effective ingredient for human fair-skin and found that the phosphorylated polysaccharides produced by lactic acid bacteria and known as antitumor substances inhibit the formation of melanin. The inventors further prepared compositions for fair-skin containing the phosphorylated polysaccharides. Thus, the object of the present invention is to provide compositions for fair-skin containing the novel effective components.

SUMMARY OF THE INVENTION

Therefore, the object of the present invention is to provide compositions for fair-skin containing the phosphorylated polysaccharides produced by lactic acid bacteria.

The phosphorylated polysaccharides used in the present invention are compounds having, for example, following structural formulae (I) and (II)

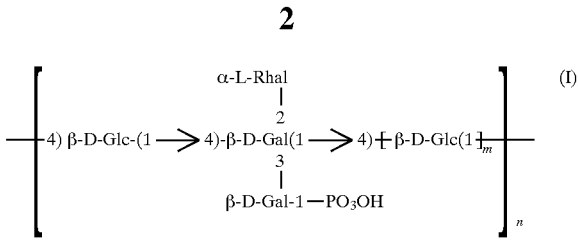

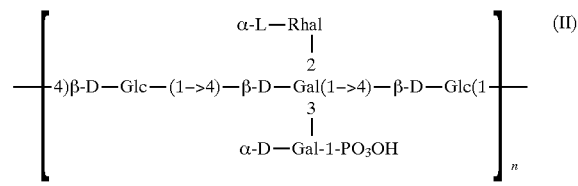

(wherein, Glc, Gal and Rha represent glucose, galactose and rhamnose residues, respectively. Numerals shown by other than subscript represent the respective binding sites, m represents integers of 0–3, and n represents the degree of polymerization of 1,000–5,000).

(wherein, Glc, Gal and Rha represent glucose, galactose and rhamnose residues, respectively. Numerals shown by other than subscript represent the respective binding sites, and n represents the degree of polymerization of 1,000–5,000).

BRIEF DESCRIPTIONS OF DRAWINGS

DETAILED DESCRIPTION AND PREFERRED EMBODIMENTS

Figure 1:
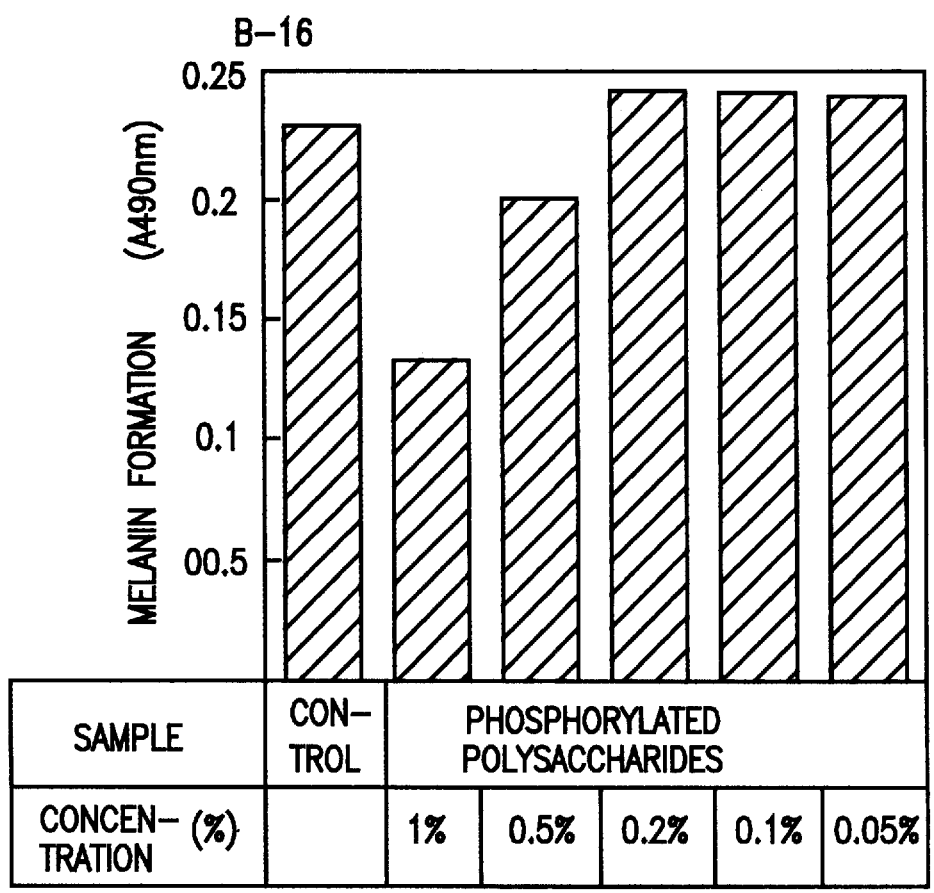
FIG. 1 represents melanin formation inhibitory effect of the phosphorylated polysaccharides in the test example 1.

The phosphorylated polysaccharides which are useful as an effective ingredient for the fair-skin composition of the present invention produced by lactic acid bacteria are known compounds (Japanese published unexamined patent application No. 229702 (1991); Nakajima et al., Carbohydr. Res., 224, pp. 245–253 (1992); WO94/12656). These compounds include those shown by above mentioned formulae (I) and (II).

The phosphorylated polysaccharides can be isolated from cultured products prepared by culture of lactococci such as *Streptococcus lactis, Lactococcus lactis, Streptococcus cremoris* or *Lactococcus cremoris* and lactobacilli such as *Lactobacillus sake*.

In the present invention, the phosphorylated polysaccharides are employed as effective ingredients for the fair-skin compositions in an amount of at least 0.001 weight % or over, preferably 0.01–20 weight % in the compositions.

The fair-skin compositions containing the phosphorylated polysaccharides as effective ingredients can be used together with conventional cosmetic bases and made in suitable forms such as creams, emulsions and toilet lotions. In addition, the other melanin synthesis inhibitors such as ultraviolet ray absorbing or scattering agents and arbutin, and the other optional additives including pharmaceutically effective components, thickening agents, plasticizers, colors and perfumes may be added.

The phosphorylated polysaccharides as an effective ingredient for fair-skin compositions of the present invention exhibit no toxicity, irritability or adverse reaction to skin.

The fair-skin compositions containing the phosphorylated polysaccharides of the present invention, inhibit the formation of melanin without effecting skin cells and provide fair-skin, thus are very useful for aesthetic compositions for fair-skin.

The present invention will be explained by the process for the preparation of the phosphorylated polysaccharides and melanin formation inhibitory effects thereof by the reference example and test examples. Further, the present invention will be practically explained by the following examples.

These examples, however, are described for explanation of the present invention and do not restrict the scope of the present invention.

Reference Example 1

The phosphorylated polysaccharides were prepared according to the procedures described in Japanese Laid-open Patent Application No. 229702 (1991). That is, completely hydrolyzed skimmed milk with actinase E was treated with an ultrafiltration membrane and the resultant retentate was used as the culture medium. In 10 L volume jar fermenters, 9.8 L each of sterilized culture medium was dividedly poured. In the medium, a pre-cultured mixture of *Streptococcus cremoris* SBT-0495 (FERM P-10053) was inoculated at a rate of 5%, and cultured at 20° C. for 24 hrs. The pH was maintained at 5.5 by the addition of ammonia water. After the culture, the cultured mixture was centrifuged to give a supernatant. The supernatant was mixed with equal volume of ethanol to give and recover a precipitate. The recovered precipitate was dissolved in 0.2N aqueous sodium chloride solution and re-precipitated by addition of ethanol. The collected precipitate was subjected to preparative SDS-gel electrophoresis to recover fractions which do not permeate in the gel. The recovered fraction was dialyzed and purified by an ion exchange chromatography using DEAE-Toyopearl 650M to obtain phosphorylated polysaccharides as an adsorbed fraction. The fraction was lyophilized to give 700 mg of the phosphorylated polysaccharides powder.

Test Example 1

Melanin formation inhibitory effect was determined using the phosphorylated polysaccharides obtained by the Reference example 1. In each well of a 96-well culture plate, 50 $\mu$l of mouse melanoma B16 cells containing $1\times10^4$ cells/ml were inoculated and cultured at 37° C. for 72 hrs. in 5% $CO_2$ atmosphere. Then, the phosphorylated polysaccharides solution was adjusted to 500 $\mu$M with Dulbecco's modified Eagle's medium (DMEM) containing 10% fetal calf serum (FCS), followed by two-fold serial dilution method to prepare the phosphorylated polysaccharides solutions. These solutions were poured 50 $\mu$l each in the wells and incubated at 37° C. for 7–14 days in 5% $CO_2$ atmosphere. After 7–14 days, the absorbance was determined for each well with the addition of the phosphorylated polysaccharides at various concentrations comparing with those of control group with the addition of sole DMEM. The melanin formation inhibitory rate was calculated by the following equation.

Inhibitory rate (%)={1−(absorbance rate of sample/absorbance of control)}×100

The results are shown in FIG. 1. The melanin formation inhibitory rate was 43.1% and 13.8% for the sample which contained the phosphorylated polysaccharides at a concentration of 1% and 0.5%, respectively. Therefore, the melanin formation inhibitory effect of the phosphorylated polysaccharides can be expected.

Test Example 2

Melanoma cell proliferation inhibitory effect was determined using the phosphorylated polysaccharides prepared by the Reference example 1. In each well of a 96-well culture plate, 50 $\mu$l of mouse melanoma B16 cells and human fetal lung fibroblast cells IMR-90 containing $1\times10^4$ cells/ml were inoculated, respectively, and incubated at 37° C. for 72 hrs. in 5% $CO_2$ atmosphere. Then, Dulbecco's modified Eagle's medium (DMEM) containing 10% fetal calf serum (FCS) was added to make 500 $\mu$M of the phosphorylated polysaccharides solutions. Then, the solutions were diluted by two-fold serial dilution method with DMEM to prepare the phosphorylated polysaccharides solutions. These solutions were poured 50 $\mu$l each in the wells and incubated at 37° C. for 7–14 days in 5% $CO_2$ atmosphere. After 7–14 days, cell proliferation activity was determined by colorimetry using a cell proliferation determination kit (Cell titer 96AQ non-radioactive cell proliferation assay, Promega Corp.).

Figure 2:
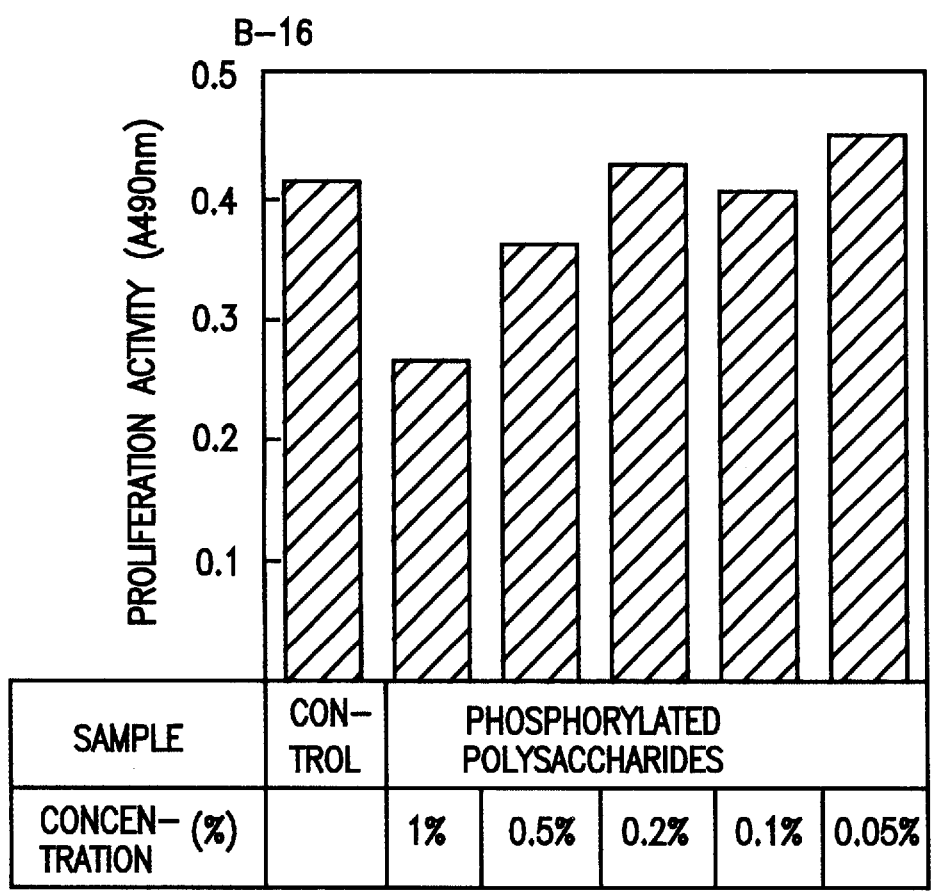
FIG. 2 represents cell proliferation inhibitory activity to mouse melanoma B16 cells with the phosphorylated polysaccharides in the test example 2.
Figure 3:
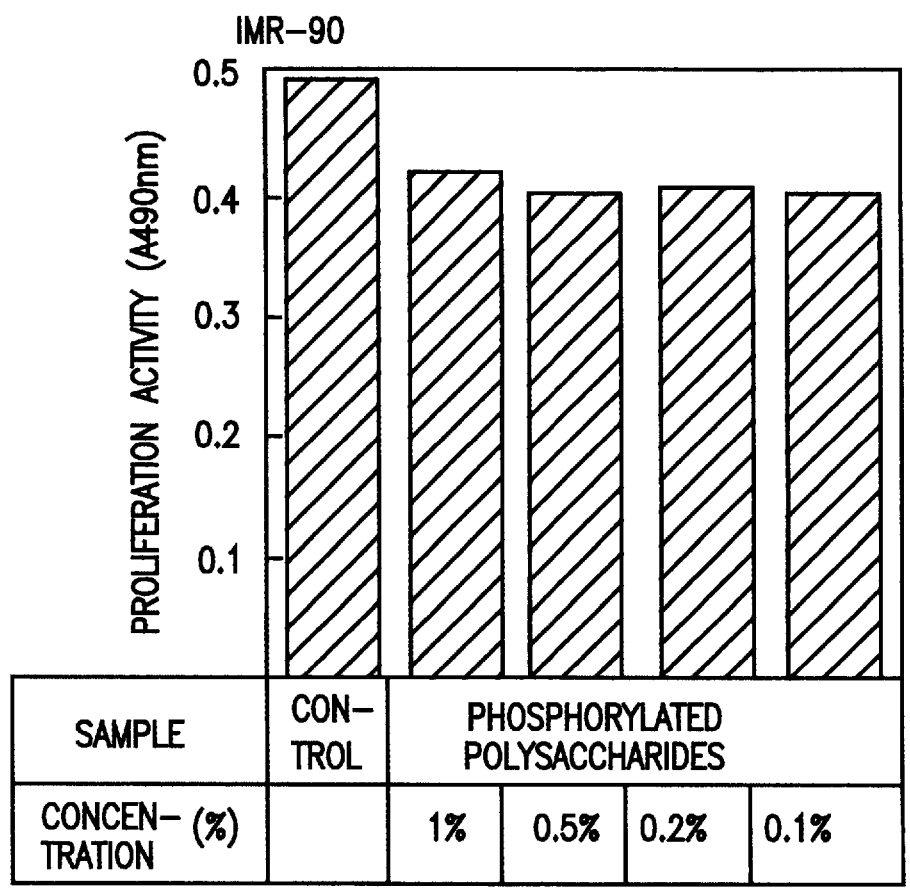
FIG. 3 represents cell proliferation inhibitory activity to human fetal lung fibroblast IMR-90 cells with the phosphorylated polysaccharides in the test example 2.

The results for mouse melanoma B16 cells and human fetal lung fibroblast IMR-90 cells are shown in FIG. 2 and 3, respectively. In mouse melanoma B16 cells, cell proliferation inhibitory rate was 33.5% and 15.0% for the sample with addition of the phosphorylated polysaccharides at a concentration of 1% and 0.5%, respectively. While, in human fetal lung fibroblast IMR-90 cells, no cell proliferation inhibitory effect dependent on the concentration of the phosphorylated polysaccharides was obtained. Therefore, the melanin formation inhibitory effect of the phosphorylated polysaccharides was clearly due to specific inhibition of proliferation of melanoma cells.

Example 1

In an aqueous solution composed 3.0 g of 70% sorbitol, 5.0 g of glycerin, 0.2 g of the phosphorylated polysaccharides and 70.0 g of water, 0.1 g of allantoin, 0.5 g of a polyoxyethylene hydrogenated castor oil derivative, 20.0 g of ethanol and a small amount of perfume were added with stirring to give a homogenous solution for an oily toilet lotion having fair-skin effect.

Example 2

In an aqueous solution composed of 2.5 g of ethylene glycol, 5.0 g of propylene glycol, 0.0001 g of silicone, 0.05 g of the phosphorylated polysaccharides and 70.0 g of water, 1.0 g of urea, 1.2 g of polyoxyethylene sorbitan monolaurate, 20.0 g of ethanol, 0.1 g of $\epsilon$-aminocaproic acid and a small amount of perfume were added with stirring to give a homogenous solution for a drying toilet lotion having fair-skin effect.

Example 3

A mixture of 2.0 g of glycerin, 20.0 g of stearic acid, 10.0 g of myristic acid, 5.0 g of lauric acid, 1.0 g of polyoxyethylene lauryl ether, 0.1 g of the phosphorylated polysaccharides, and a small amount of a perfume and an antiseptic was heated to 75° C. to give a melted mixture. Then, 5.5 g of potassium hydroxide and 56.0 g of water were added with stirring and the resultant mixture was cooled to give a cleansing cream having fair-skin effect.

Example 4

A mixture of 10.0 g of beeswax, 6.0 g of paraffin wax, 3.0 g of lanolin, 6.0 g of isopropyl myristate, 8.0 g of squalane, 25.0 g of liquid paraffin, 0.5 g of the phosphorylated polysaccharides, 1.8 g of a polyoxyethylene sorbitan monostearate, 4.2 g of sorbitan monostearate and a small amount of an antiseptic was heated to 75° C. to give a melted mixture. Then, 2.0 g of propylene glycol, 0.7 g of borax, 5.0 g of urea and 28.0 g of water were added to the melted mixture with stirring, cooled and a small amount of perfume was added to give an oily cream having fair-skin effect.

We claim:

1. A composition for inhibiting the formation of melanin in humans with fair-skin comprised of a cosmetic base and phosphorylated polysaccharides produced by lactic acid bacteria as an effective ingredient.

2. The composition for fair-skin according to claim 1, wherein said phosphorylated polysaccharides are shown by the following formula (I)

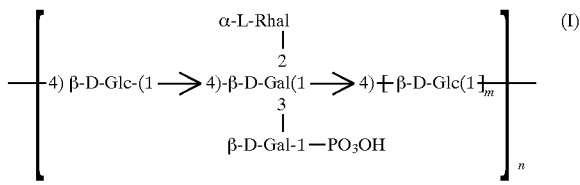

(wherein, Glc, Gal and Rha represent glucose, galactose and rhamnose residues, respectively, numerals shown by other than subscript represent the respective binding sites, m represents integers of 0–3, and n represents the degree of polymerization of 1,000–5,000).

3. The composition for fair-skin according to claim 1, wherein said phosphorylated polysaccharides are shown by the following formula (II)

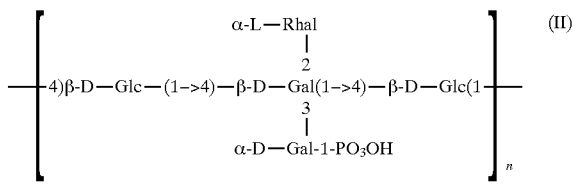

(wherein, Glc, Gal and Rha represent glucose, galactose and rhamnose residues, respectively. Numerals shown by other than subscript represent the respective binding sites, and n represents the degree of polymerization of 1,000–5,000).

4. The composition for fair-skin according to claim 1, wherein said composition contains at least 0.001 weight % or over, of the phosphorylated polysaccharides as an effective ingredient.

5. The composition for fair-skin according to claim 1, wherein said composition contains 0.01–20 weight % of the phosphorylated polysaccharides as an effective ingredient.

6. A process for inhibiting the formation of melanin in humans with fair skin which comprises applying to the skin a melanin formation inhibiting amount of the composition of claim 1.

7. The process of claim 6 wherein the phosphorylated polysaccharides are shown by the following formula (I)

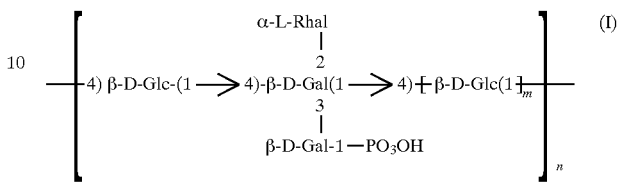

(wherein, Glc, Gal and Rha represent glucose, galactose and rhamnose residues, respectively, numerals shown by other than subscript represent the respective binding sites, m represents integers of 0–3, and n represents the degree of polymerization of 1,000–5,000).

8. The process of claim 6, wherein the phosphorylated polysaccharides are shown by the following formula (II)

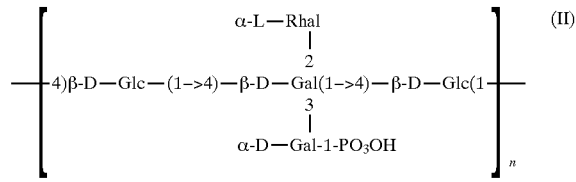

(wherein, Glc, Gal and Rha represent glucose, galactose and rhamnose residues, respectively, numerals shown by other than subscript represent the respective binding sites, and n represents the degree of polymerization of 1,000–5,000).

9. The process of claim 6, wherein said composition contains at least 0.001 weight % of the phosphorylated polysaccharides as an effective ingredient.

10. The process of claim 6 wherein the composition contains 0.01–20 weight % of the phosphorylated polysaccharides as an effective ingredient.

* * * * *